(12) United States Patent
Kafer et al.

(10) Patent No.: US 12,309,555 B2
(45) Date of Patent: May 20, 2025

(54) SYSTEMS AND METHODS FOR CONDUCTING AND VALIDATING AN AUDIOMETRIC TEST

(71) Applicant: Examinetics, Inc., Overland Park, KS (US)

(72) Inventors: Matthew Peter Kafer, Belton, MO (US); Cassandra Lynn Ford, Kansas City, MO (US); Edward Henry Stratemeier, IV, Prairie Village, KS (US)

(73) Assignee: Examinetics, Inc., Overland Park, KS (US)

( * ) Notice: Subject to any disclaimer, the term of this patent is extended or adjusted under 35 U.S.C. 154(b) by 246 days.

(21) Appl. No.: 18/137,375

(22) Filed: Apr. 20, 2023

(65) Prior Publication Data

US 2024/0357302 A1    Oct. 24, 2024

(51) Int. Cl.
*H04R 29/00* (2006.01)
*G10L 13/08* (2013.01)

(52) U.S. Cl.
CPC ............ *H04R 29/001* (2013.01); *G10L 13/08* (2013.01); *H04R 29/008* (2013.01)

(58) Field of Classification Search
CPC .... H04R 29/00; H04R 29/008; H04R 29/001; A61B 5/12; A61B 5/6803
USPC ................................................ 381/56–60, 74
See application file for complete search history.

(56) References Cited

U.S. PATENT DOCUMENTS

| | | | |
|---|---|---|---|
| 7,190,795 B2 * | 3/2007 | Simon ..................... | A61B 5/121 381/60 |
| 9,265,660 B2 * | 2/2016 | Kilgard ................... | G09B 23/28 |
| 9,301,714 B2 * | 4/2016 | Baker ...................... | H04R 25/50 |
| 10,888,253 B2 * | 1/2021 | Hamanaka ............ | H04R 1/1008 |
| 11,501,875 B1 | 11/2022 | Kloster et al. | |
| 2013/0274628 A1 | 10/2013 | Fausti et al. | |
| 2015/0023534 A1 | 1/2015 | Shennib | |
| 2019/0175011 A1 | 6/2019 | Jensen et al. | |
| 2020/0178852 A1 * | 6/2020 | Lardaro ................. | G16H 40/67 |
| 2024/0324909 A1 * | 10/2024 | Milne .................... | A61B 5/123 |

* cited by examiner

*Primary Examiner* — Disler Paul
(74) *Attorney, Agent, or Firm* — Kory D. Christensen

(57) ABSTRACT

A computer-implemented method for conducting an audiometric test using an audiometer includes confirming that a room in which the audiometric test is to be administered has a set of background sound pressure levels that conform to a predetermined standard; determining that the audiometer has been calibrated at least once on a day in which the audiometric test is to be administered; displaying instructions to a subject for taking the audiometric test; and conducting the audiometric test of the subject using a mobile device in electronic communication the audiometer, wherein the mobile device is separate from and controls the audiometer, and wherein conducting the audiometric test is blocked until the steps of confirming, determining, and displaying have been performed.

39 Claims, 10 Drawing Sheets

SYSTEMS AND METHODS FOR CONDUCTING AND VALIDATING AN AUDIOMETRIC TEST

TECHNICAL FIELD

The present disclosure relates to audiometric testing and, more particularly, to systems and methods for conducting a valid audiometric test.

BACKGROUND

Audiometers for conducting audiometric tests (i.e., standardized hearing tests) can be expensive and difficult to transport. For example, a typical audiometer may cost thousands of dollars and be too heavy or bulky to easily move between testing sites, forcing those desiring an audiometric test to travel to the fixed location of the audiometer. This is inconvenient and unsuitable to on-site testing, such as testing employees to comply with Occupational Safety and Health Administration (OSHA) regulations.

Furthermore, even expensive audiometers may produce invalid results. For example, background noise can make it difficult for a subject to hear tones produced by the audiometer. Moreover, the audiometer and/or a headset used by the audiometer can become uncalibrated, producing tones that diverge in frequency and/or sound pressure levels from standard test tones. In addition, subjects of an audiometric test may not be properly instructed on taking the test, resulting in user error and preventing hearing threshold levels from being determined or producing incorrect hearing threshold levels. Invalid tests cannot be used to satisfy the regulations of OSHA or other organizations and may result in adverse consequences for a business due to non-compliance.

What is needed is a system and method for conducting and/or certifying a valid audiometric test that overcomes one or more of the foregoing issues.

SUMMARY OF THE DISCLOSURE

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

According to one aspect, a system for conducting an audiometric test includes an audiometer and a mobile device in electronic communication with the audiometer, where the audiometer and the mobile device are separate devices. The mobile device includes a display screen, one or more processors, and a memory storing program code that causes the one or more processors to perform a method. The method includes confirming that a room in which the audiometric test is to be administered has a set of background sound pressure levels that conform to a predetermined standard. The method also includes determining that a calibration of the audiometer has been validated at least once on a day (or other time period) in which the audiometric test is to be administered. In addition, the method includes conducting the audiometric test of the subject using the mobile device to control the audiometer, where conducting the audiometric test is blocked until the one or more processors have (1) confirmed that the room in which the audiometric test is to be administered has the set of background sound pressure levels that conform to the predetermined standard and (2) determined that a calibration of the audiometer has been validated at least once on the day in which the audiometric test is to be administered.

In an example, the audiometer includes a tone generator electronically connected to a headset, and the one or more processors, in response to the calibration of the audiometer not having been validated at least once on the day in which the audiometric test is to be administered, are to sample audio output of the headset at each a plurality of test tones generated by the tone generator and determine that the audio output of the headset deviates from each of the plurality of test tones by no more than a threshold decibel level. In some examples, the system further comprises a calibrator including a housing and two microphones positioned on opposite sides of the housing, the microphones being configured to be placed in proximity to respective drivers of the headset when the audio output of the headset is being sampled

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures relating to one or more embodiments, in which.

DETAILED DESCRIPTION

Figure 1:
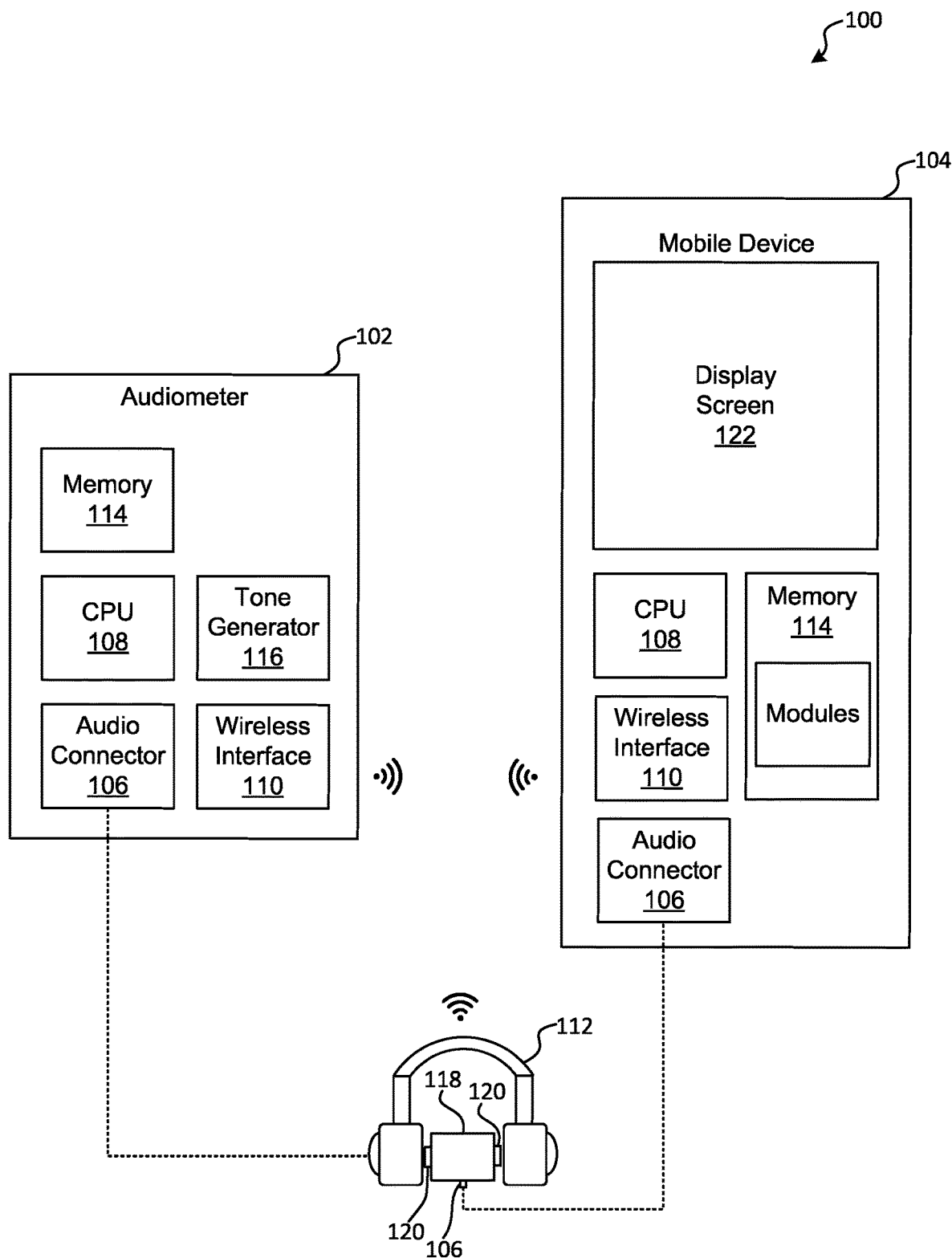
FIG. 1 is a schematic block diagram of a system for conducting an audiometric test according to an embodiment.

In the following Detailed Description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 is a schematic diagram of an exemplary system 100 for conducting a valid audiometric test. The system 100 may include an audiometer 102 and a mobile device 104 for controlling the audiometer 102. As illustrated, the audiometer 102 and the mobile device 104 may be separate devices that communicate with each other through wireless or wired connections.

The audiometer 102 may include one or more audio connectors 106, which may be embodied as physical audio ports/jacks, e.g., 3.5 mm female audio jacks, as well as audio circuitry, e.g., Analog-to-Digital Converters (ADCs), Digital-to-Analog Converters (DACs), filters, or the like, for communicating digital data to and from a CPU 108. Alternatively, or in addition, the audiometer 102 may include a wireless interface 110 for transmitting and receiving data (e.g., audio, messages) to and from the mobile device 104 and/or a headset 112. The wireless interface 110 may implement one or more wireless standards, including, without limitation, Bluetooth, Wi-Fi (802.11), ZigBee, or Z-Wave.

The headset 112 may be embodied as headphones, earbuds, or the like, which include a pair of small loudspeaker drivers worn on or around the head over a user's ears. The drivers are electroacoustic transducers that convert an electrical signal to a corresponding sound. Suitable headsets for use in conducting an audiometric test include a DD65v2 headset, available from RadioEar.

The CPU 108 may be any suitable microprocessor, microcontroller, Digital Signal Processor (DSP), Field Programmable Gate Array (FPGA) or other device that may execute, for example, instructions stored in a memory 114. The memory 114 may be implemented using any suitable combination of Random Access Memory (RAM), Read-Only Memory (ROM), Electrically Erasable Programmable Read-Only Memory (EEPROM), or the like.

In one embodiment, the audiometer 102 includes a tone generator 116 that generates, for example, standardized tones on the headset 112. The tone generator 116 may include, for example, a 32-bit DAC, filters, and/or other circuitry needed for generating analog audio output via the audio connector 106. A suitable tone generator 116 may include, for example, an ES9218 DAC available from EES and a STM32 processor available from STMicroelectronics. In some embodiments, including fully wireless embodiments, the functionality of the tone generator 116 may be incorporated into the CPU 108. However, for clarity, the tone generator 116 is illustrated as a separate component.

In some embodiments, the headset 112 and audiometer 102 may be calibrated using a calibrator 118, as described in greater detail in connection with FIG. 6. The calibrator 118 may include a housing having a width that approximates a distance between a person's ears. Further, the calibrator 118 may include one or more microphones 120. Suitable microphones 120 may include a I437L microphone, available from MicW.

In the illustrated embodiment, two microphones 120 are provided on opposite sides of the housing in order to be placed in proximity to the left and right loudspeaker drivers of the headset 112. The calibrator 118 may also include an audio connector 106 for electrically connecting the microphones 120 to an audio connector 106 in the within the mobile device 104. Wireless communication may be used in other embodiments.

The mobile device 104 may also include a wireless interface 110, a CPU 108, and a memory 114, each of which may be the same as, or different from, the corresponding components in the audiometer 102. The memory 114 of the mobile device 104 may store various software modules as described in greater detail with respect to FIG. 2. The mobile device 104 may further include a display screen 122, such as a Liquid Crystal Display (LCD), a Light-Emitting Diode (LED) display, an Organic Light-Emitted Diode (OLED) display, or the like. In some embodiments, the mobile device 104 may be implemented using a tablet computer, such as an iPad® tablet, available from Apple Corporation.

Figure 2:
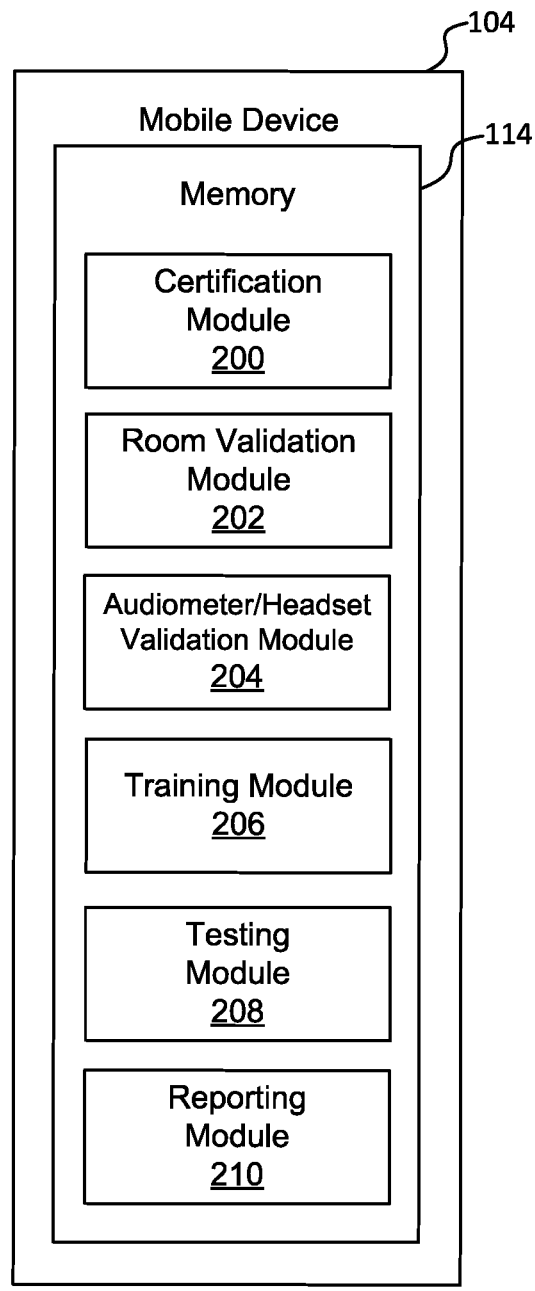
FIG. 2 is a schematic block diagram of software modules within a memory of a mobile device according to an embodiment.

Referring to FIG. 2, the memory 114 of the mobile device 104 (and, in some embodiments, the audiometer 102) may store a number of software modules that cause the CPU 108 and other hardware of the mobile device 104 (and the audiometer 102) to perform various methods disclosed herein. For example, the memory 114 may include, without limitation, a certification module 200, a room validation module 202, an audiometer/headset validation module 204, a training module 206, a testing module 208, and a reporting module 210. Those of skill in the art will recognize that the functionality of various modules may be combined and/or new modules may be added without departing from the spirit and scope of the disclosure.

As described more fully hereafter, the certification module 200 generates a user interface on the display screen 122 of FIG. 1 including indications of a room validation status and an audiometer/headset validation status. The statuses may be stored in the memory 114 of the mobile device 104 as numerical values and graphically represented within the user interface by icons, text, colors, or other means.

In one embodiment, the certification module 200 prevents the audiometric test from commencing until (1) the room in which the audiometric test is to be administered has a set of background sound pressure levels that conform to a predetermined standard and (2) the calibration of the audiometer 102 and associated headset 112 have been validated at least once on a day (or other prescribed time period) in which the audiometric test is to be administered. In some embodiments, the certification module 200 may also prevent the audiometric test from commencing until the subject has been instructed concerning the audiometric test using the training module 206, as discussed below.

The room validation module 202 confirms that the room in which the audiometric test is to be administered has a set of background sound pressure levels that conform to a predetermined standard. The audiometer/headset validation module 204 determines that the calibration of the audiometer 102 and headset 112 has been validated at least once on a day (or other period) in which the audiometric test is to be administered. In some embodiments, the audiometer/headset validation module 204 may also facilitate calibration.

The training module 206 displays instructions to a subject taking the audiometric test. The training module 206 may further display a video demonstrating one or more of the instructions for the subject. In some embodiments, the user must acknowledge viewing the instructions (and video) in order for the audiometric test to commence. In some embodiments, the training module 206 may be further used to instruct a proctor (i.e., a person administering a hearing test) on how to validate the room and/or validate the calibration of the audiometer 102 and headset 112.

The testing module 208 conducts the audiometric test of the subject using the audiometer 102 under control of the mobile device 104. In some embodiments, the audiometric test may be conducted using the Hughson-Westlake procedure. As noted above, the audiometric test is prevented (e.g., blocked, not allowed) until the room validation module 202 confirms that the room in which the audiometric test is to be administered has the set of background sound pressure levels that conform to the predetermined standard and the audiometer/headset validation module 204 determines that the audiometer 102 has been calibrated at least once on the day (or other period) in which the audiometric test is to be administered. In some embodiments, the audiometric test may be further prevented from operating until the training module 206 displays the instructions to the subject (and, in certain embodiments, the subject acknowledges that the instructions and/or video have been viewed).

The reporting module 210 may electronically report the results of the audiometric test, which may include sending at least one of an email or a text message containing or referencing (e.g., via a link) the results to one or more of the subject and an employer of the subject. The results may include an audiogram that includes, for each ear of the subject, a graph of hearing threshold levels of the subject for a set of frequencies. Each hearing threshold level may include an indication of the sound pressure level at which the subject indicated that the tone at a given frequency was heard within a predetermined time interval. According to the Hughson-Westlake procedure, a hearing threshold level is defined as the lowest decibel hearing level at which responses occur in at least one half of a series of ascending trials. The minimum number of responses according to this procedure needed to determine the threshold of hearing is two responses out of three presentations at a single level. Other procedures may be used in different embodiments.

The reporting module 210 may also generate an audible (e.g., spoken) explanation of the results using, for example, stored (sampled) audio or text-to-speech technology. Some of the data for the spoken explanation may be obtained from the results of the audiometric test (e.g., hearing thresholds), while other data may be stored as one or more scripts or templates. In some embodiments, the reporting module 210 may be required to provide an explanation (spoken or otherwise) if there is a change in the subject's hearing or the subject's hearing is below a threshold standard.

Figure 3:
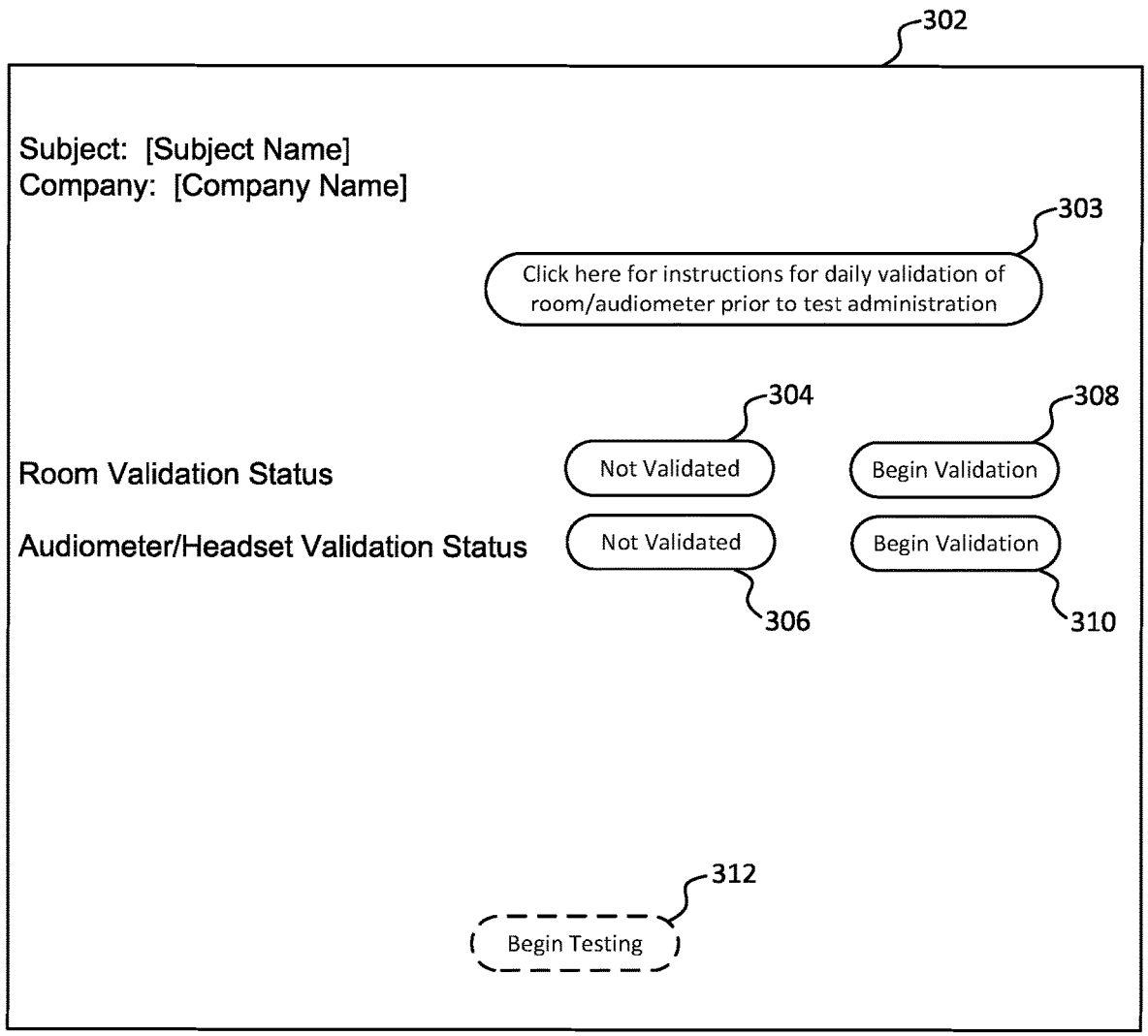
FIG. 3 is an exemplary user interface generated by a certification module according to an embodiment.

FIG. 3 is an exemplary user interface 302 generated by the certification module 200, which may be displayed on the display screen 122 of the mobile device 104 shown in FIG. 1. The user interface 302 may display the name of the subject to take audiometric test and, optionally, the subject's company (employer). In some embodiments, the name and/or company of the subject may have been previous selected or specified in a separate user interface (not shown). Furthermore, other user interfaces (not shown) may be provided for logging into the system 100, pairing the mobile device 104 with the audiometer 102, and, in some embodiments, pairing the audiometer 102 with the headset 112, using standard Bluetooth pairing or other suitable pairing procedures depending on the type of wireless interfaces 110 in use.

The user interface 302 may optionally display a control 303 for displaying instructions for daily validation of the room and/or audiometer/headset prior to test administration. Activating the control 303 may cause the training module 206 of FIG. 2 to display instructions for the test administrator (which may be the subject in some cases) on how to validate the room and/or audiometer/headset on a daily basis.

Figure 4:
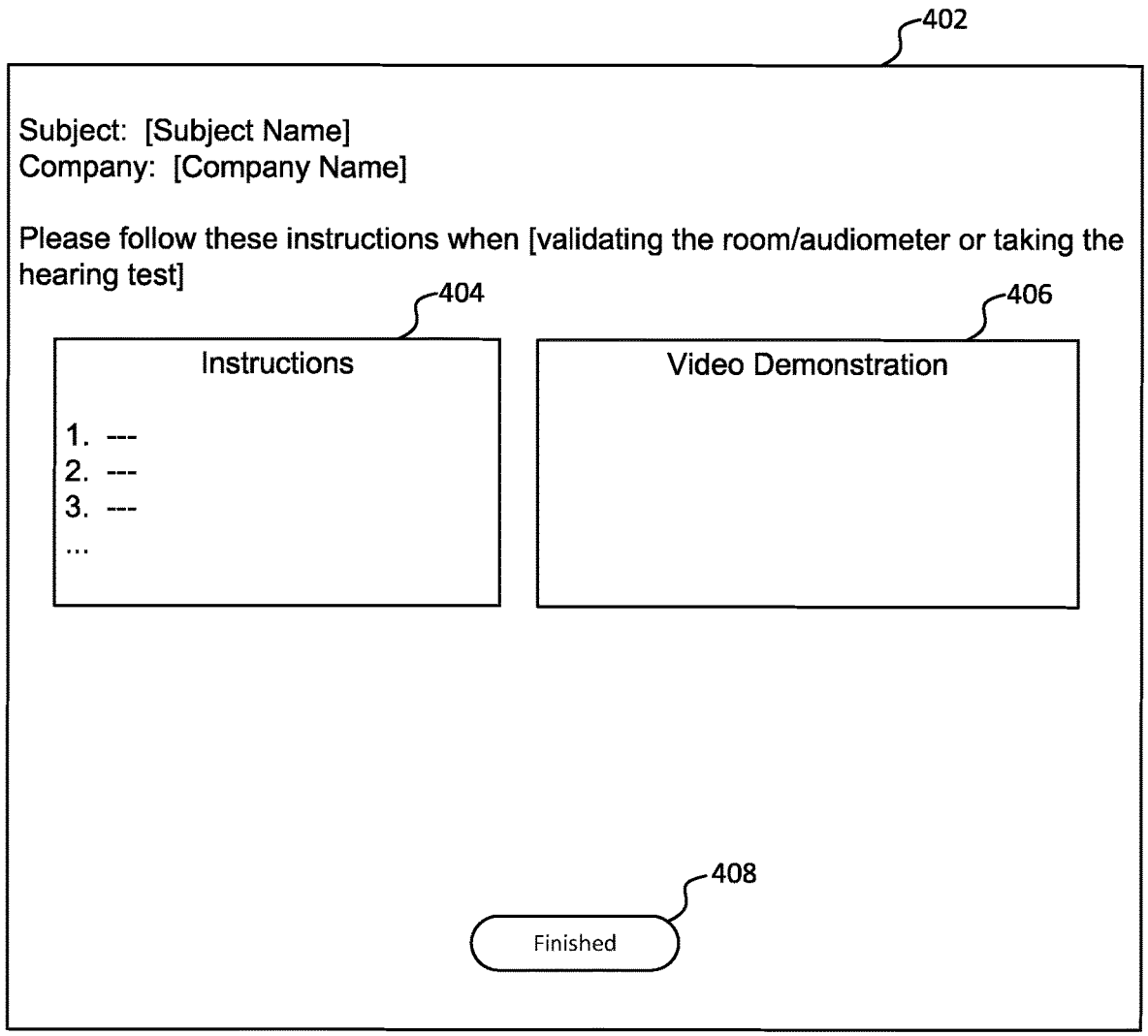
FIG. 4 is an exemplary user interface generated by an instruction module according to an embodiment.

FIG. 4 illustrates an exemplary embodiment of a user interface 402 for displaying instructions 404 to the test administrator. Alternatively or in addition, the user interface 402 may display a video demonstration 406, which may include a video depicting step-by-step instructions to the test administrator. The video demonstration 406 may be stored in the memory 114 of the mobile device 104 or streamed from a remote location via the wireless interface 110.

The instructions 404 and/or video demonstration 406 may be automatically displayed once each day (or other designated time period) and/or displayed in response to user activation of the control 301 of FIG. 3. In addition, the user interface 402 may include a control 408 by which the test administrator may acknowledge that they have reviewed the instructions 404 and/or video demonstration 406. In one embodiment, activation of the control 408 is a prerequisite for proceeding with the audiometric test.

Returning to FIG. 3, the user interface 302 may further display a room validation status 304 and an audiometer/headset validation status 306. As described more fully hereafter, the room validation status 304 may indicate whether the room in which the audiometric test is to be administered has a set of background sound pressure levels that conform to a predetermined standard. The audiometer/headset validation status 306 may indicate whether the calibration of the audiometer 102 (including the headset 112) has validated at least once on a day (or other period) in which the audiometric test is to be administered. The room validation status 304 and headset validation status 306 may be indicated using various combinations of text, graphics, colors, icons, or the like. In the example embodiment, the respective statuses 304, 306 are indicated by text, i.e., "not validated," which may be the default condition until room validation and audiometer/headset calibration have been performed.

In addition, the user interface 302 may include controls 308, 310 to initiate room validation and audiometer/headset validation, respectively. In one embodiment, activating the control 308 to initiate room validation may result in the room validation module 202 (shown in FIG. 2) being executed, while the control 310 to initiate headset validation may result in the audiometer/headset validation module 204 being executed.

As illustrated, a control 312 may be provided to begin an audiometric test, which may initiate the testing module 208 shown in FIG. 2. However, the control 312 may be deactivated (e.g., greyed-out, not shown) until at least (1) the room in which the audiometric test is to be administered has a set of background sound pressure levels that conform to a predetermined standard and (2) the calibration of the audiometer 102 (including the headset 112) has been validated at least once on a day (or other period) in which the audiometric test is to be administered.

In one embodiment, the control 312 to begin testing may also be deactivated until the subject has been instructed on taking the audiometric test. In many instances, errors made by the subject may invalidate the audiometric test, preventing hearing threshold levels from being determined or producing incorrect hearing threshold levels. Accordingly, the user interface 402 of FIG. 4 may be used for instructing the subject on taking the audiometric test. The user interface 402 may include instructions 404, which may include step-by-step written, spoken and/or visually illustrated instructions. For example, the instructions 404 may include the following:

1. You will hear a series of tones during your test. As soon as you hear a tone, tap the "I Heard" button on your device.
2. Some of the tones you will hear will be very quiet. Please tap the "I Heard" button if you just barely hear the tone.
3. Missing a tone will not impact the outcome of the test. If you are distracted by a brief noise, don't worry. You will have more than one opportunity to respond to each tone.
4. After completion of your test, you will be shown a graph and hear an explanation of your test results.

5. Please remove hearing aids, glasses, earrings, or anything else you may be wearing between your head and the headphones, then place the headphones back over your ears.

6. When you are finished, click the "Finished" button.

The user interface 402 may further include a video demonstration 406 that illustrates and/or demonstrates one or more of the instructions 404 to the subject. A video stream displayed as the video demonstration 406 may be stored in the memory 114 and/or accessed from a remote source (server) using the wireless interface 110.

In addition, the control 408 in the user interface 402 may be used by the subject to acknowledge that they have reviewed the instructions 404 and/or video demonstration 406. In one embodiment, activation of the control 408 is a prerequisite for activating the control 312 in FIG. 3 for beginning the audiometric test.

Returning to FIG. 3, if the room in which the test is to be given has not yet been validated (i.e., the room has a set of background sound pressure levels that conform to a predetermined standard), a proctor (or other individual overseeing the test) or, in some cases, the subject, may activate the control 308 of FIG. 3 to begin room validation, which may result in execution of the room validation module 202 of FIG. 2, although, in some embodiments, the room validation module 202 may be executed automatically without activation of the control 308.

An exemplary standard for the set of background pressure levels is shown below in Table 1. As illustrated, a plurality of octave-band center frequencies (measured in Hertz) may have corresponding maximum sound pressure levels (measured in dB). For example, in order for the room to be validated, at 500 Hz, the maximum sound pressure level is 40 dB, while at 2000 Hz, the maximum sound pressure level is 47 dB.

TABLE 1

| | Octave-band center frequency (Hz) | | | | |
|---|---|---|---|---|---|
| | 500 | 1000 | 2000 | 4000 | 8000 |
| Maximum sound pressure level (dB) | 40 | 40 | 47 | 57 | 62 |

Figure 5:
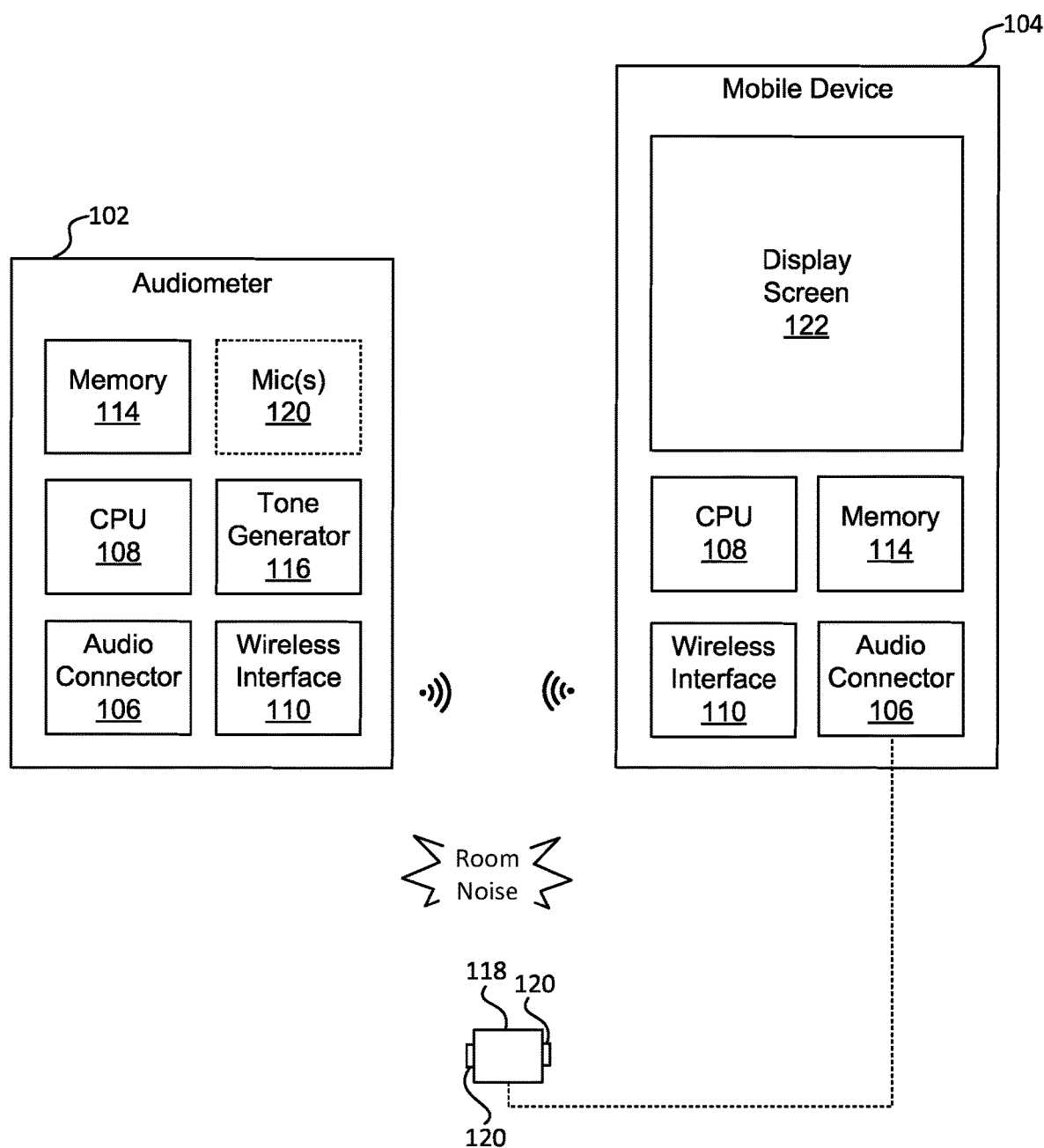
FIG. 5 is a schematic block diagram of a hardware configuration for validating a room according to an embodiment.

FIG. 5 illustrates a hardware configuration for confirming that the room in which the audiometric test is to be administered has a set of background sound pressure levels that conform to a predetermined standard. Determining the set of background sound pressure levels may be performed, in one embodiment, using the microphone(s) 120 associated with the calibrator 118. Alternatively, the audiometer 102, itself, and/or the mobile device 104 may have microphones that may be used for this purpose.

Sound captured by the microphone(s) 120, which includes ambient noise in the room, may be conveyed to the mobile device 104 via the audio connector 106 (or wirelessly) where it is deconstructed using, e.g., Fourier analysis, and evaluated at each of the octave-band center frequencies shown in Table 1. If the sound pressure level for one or more of the octave-band center frequencies exceeds the corresponding maximum sound pressure levels, the room may not be validated. In such a case, the user may be prompted by the room validation module 202 to move the system 100 to a quieter environment, remove or deactivate noisy equipment, and/or take other remedial action.

When it is confirmed that the room in which the audiometric test is to be administered has a set of background sound pressure levels that conform to a predetermined standard, the room validation status 304 shown in FIG. 3 may be changed by the room validation module 202 to indicate that the room is validated, either by a change in text, graphics, color, icon, or the like.

Typically, audiometric testing equipment is calibrated at regular intervals, such that the tones generated by the tone generator 116 and reproduced by the headset 112 have frequencies and sound pressure levels that conform to a predetermined standard. However, between these intervals, it is possible that the audiometer 102 and/or the headset 112 may fall out of calibration.

Returning to FIG. 3, if the calibration of the audiometer 102 and headset 112 has not been validated at least once on the day of the audiometric test, the proctor (or other individual overseeing the test) or, in some cases, the subject, may activate the control 310 of FIG. 3 to begin audiometer/headset validation, which may result in execution of the audiometer/headset validation module 204 of FIG. 2 (in some embodiments, the audiometer/headset validation module 204 may be executed automatically without activation of the control 310).

Figure 6:
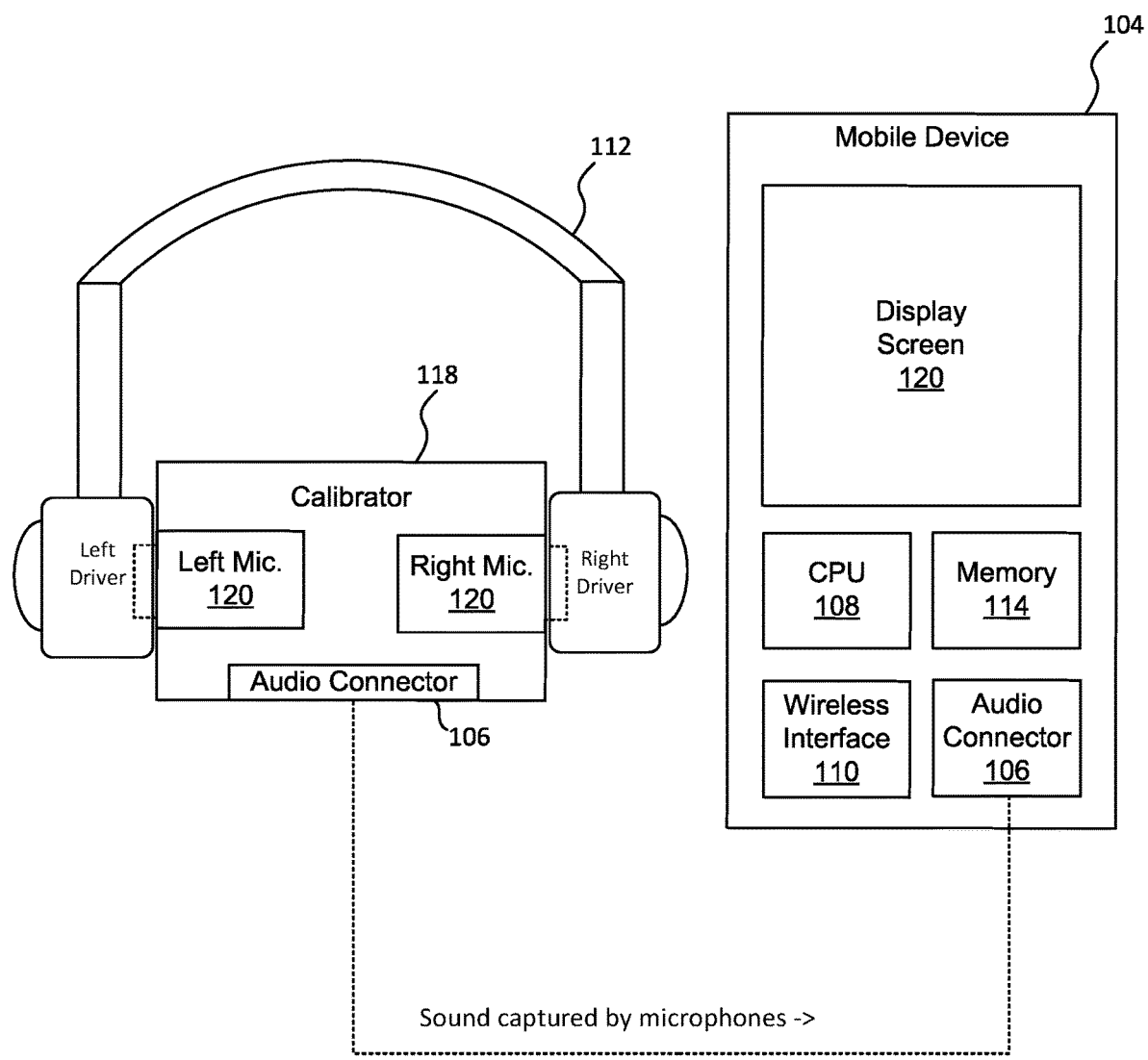
FIG. 6 is a schematic block diagram of a hardware configuration for validating an audiometer and associated headset according to an embodiment.

FIG. 6 illustrates a hardware configuration for calibrating the audiometer 102 and headset 112 using the calibrator 118 when the calibration has not been validated within the day (or other time period) in which the audiometric test is to be conducted. As shown, the calibrator 118 may include left and right microphones 120 in one embodiment, which correspond to the left and right drivers of the headset 112, respectively. In some embodiments, the housing of the calibrator 118 has a width that approximates the width of a human head. The headset 112 may be physically placed such that the left driver of the headset 112 is in proximity to left microphone 120 and the right driver of the headset 112 is in proximity to right microphone 120. In some embodiments, the left and right microphones 120 may slightly protrude from the calibrator 118 and be covered by the left and right drivers of the headset 112 in the manner of human ears, replicating the experience of a human wearing the headset 112.

During calibration, the mobile device 104 controls the audiometer 102 in the same manner as an audiometric test (as described more fully below) to generate a series of test tones at various frequencies in each of the left and right drivers of the headset 112. In response, the left microphone 120 and the right microphone 120 of the audiometer 102 will sample the sound produced by the audiometer 102 and output by the headset 112 to determine whether the sampled tones deviate from the test tones by no more than a threshold decibel level. In one embodiment, the threshold decibel level is 10 dB, and the plurality of test tones may be selected from 500 Hz, 1000 Hz, 2000 Hz, 3000 Hz, 4000 Hz, 6000 Hz, and 8000 Hz, which correspond to the tones typically used during audiometric testing.

As in the case of room validation, sound captured by the microphones 120 may be conveyed in analog or digital format to the mobile device 104, where the waveform (frequency and amplitude) of each sampled test tone is analyzed. If the sound pressure level (amplitude) for any test tone differs by more than 10 dB from the expected level, the audiometer 102 and headset 112 may fail validation and the proctor conducting the test may be informed via the display screen 122 so that remedial action may be taken, including, but not limited to, checking connections and/or replacing audiometer 102 and/or the headset 112.

In some embodiments, the audiometer 102 and headset 112 may need to be calibrated, such that the headset 112 outputs a louder (or softer) volume at the frequency where validation failed. If the louder (or softer) tone resolves the issue, the mobile device 104 and/or the audiometer 102 may store the amount of the increase (or decrease) in volume in an equalization table in the memory 114 that will be utilized during the subsequent audiometric test. If the calibration cannot be accomplished, the proctor may be prompted to take more drastic remedial action, such as replacing the headset 112 and/or the audiometer 102.

In some embodiments, a calibrator 118 may not be used. For example, the drivers of the headset 112 may be brought in proximity to one or more microphones 120 within the audiometer 102 or the mobile device 104. In other embodiments, the mobile device 104 may be coupled via wires (or wirelessly) to microphones 120 that may be individually placed in proximity (e.g., inserted into) to the left and right drivers of the headset 112.

Figure 7:
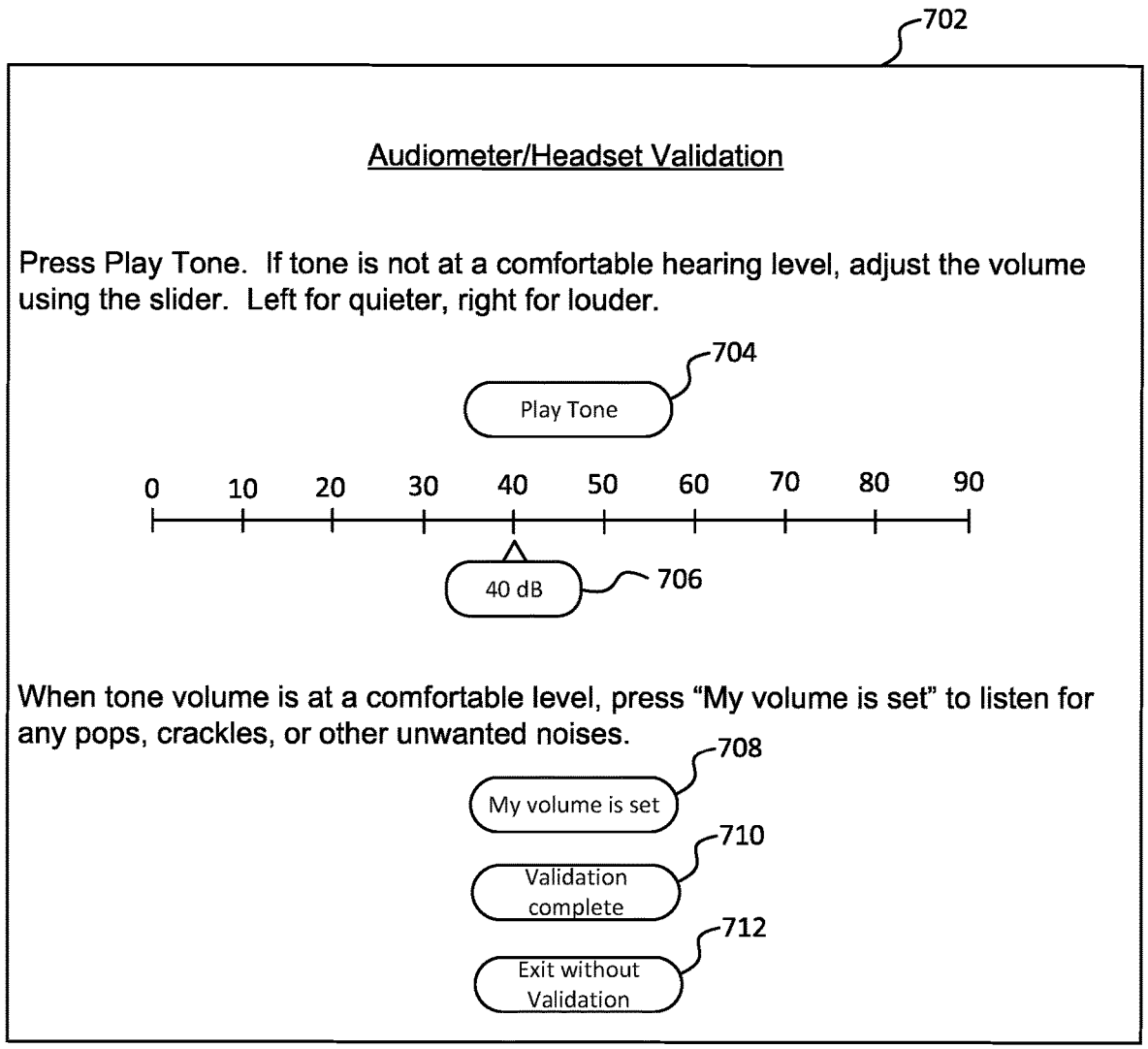
FIG. 7 is an exemplary user interface generated by audiometer/headset validation module according to an embodiment.

In an alternative embodiment or as an additional aspect of validating the calibration of the audiometer 102 and headset 112, a user interface 702 as shown in FIG. 7 may be generated by the audiometer/headset validation module 204. The user interface 702 may instruct a user (such as the proctor or, in some cases, the subject) to activate a control 704 to play a tone at a predetermined frequency and volume. If the volume is too soft or uncomfortably loud, the user may be allowed to move a slider 706 to select a comfortable volume.

Once the volume has been set, the user may activate a control 708 (e.g., "My volume is set") which causes a set of tones to be played during which the user may listen for any pops, crackles, or other unwanted noises, which may be indicative of a bad physical connection between the headset 112 and the audiometer 102 and/or interference with a wireless connection. If no unwanted sounds are heard, the user may activate a control 710 to indicate that validation is complete, which may result in the user interface of FIG. 3 being re-displayed with an updated audiometer/headset validation status 306, i.e., the audiometer/headset are "validated." Alternatively, the user may activate a different control 712 to exit without validation, which will likewise invoke the certification module 200 and display the user interface 302 of FIG. 3. However, because the audiometer 102 and headset 112 are not validated, the control 312 to begin testing will still be inactive.

Figure 8:
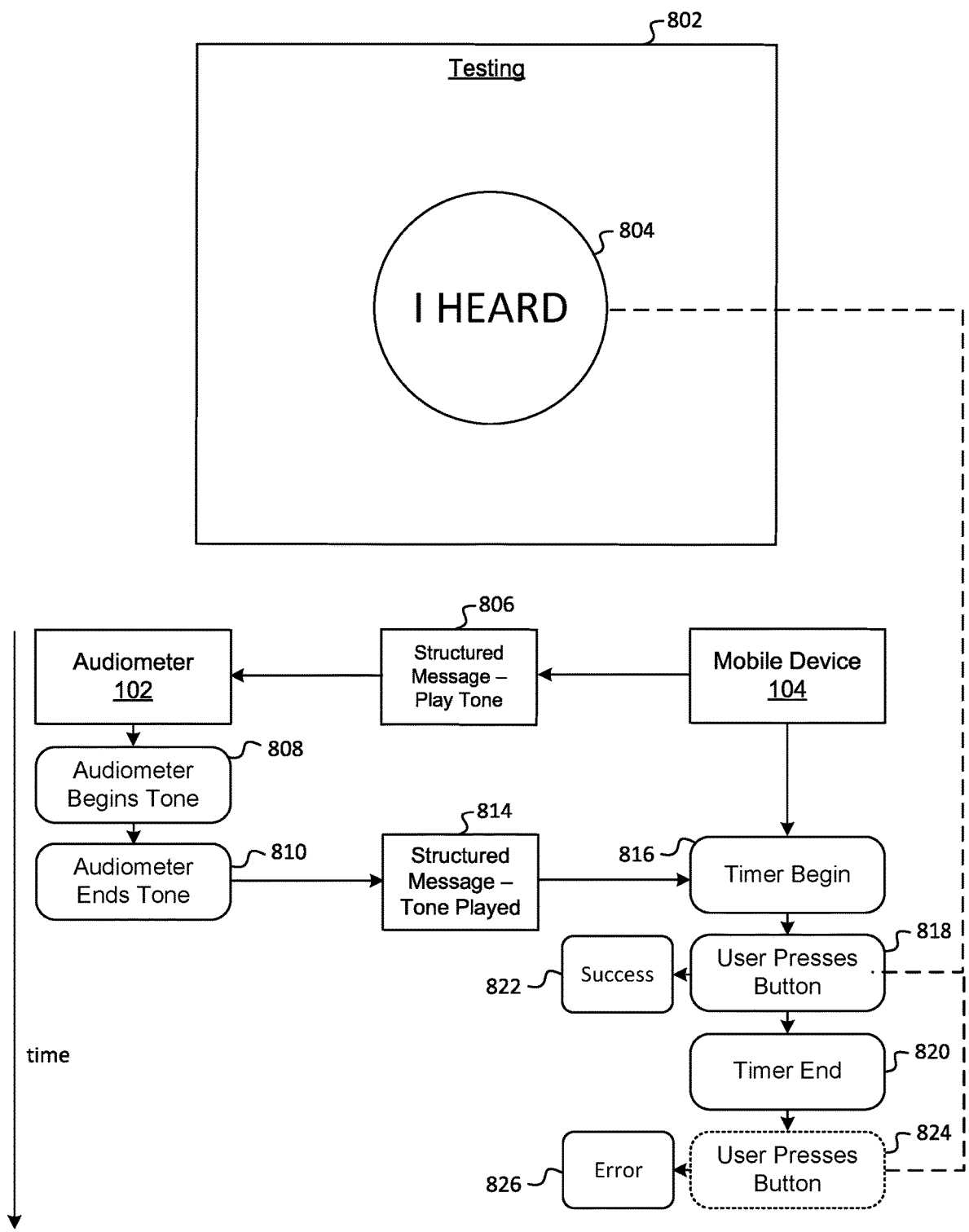
FIG. 8 is an exemplary user interface generated by a testing module and a dataflow diagram of a testing procedure according to an embodiment.

Once validation for both the room and the audiometer 102 has been completed, the user may activate the control 312 to begin the audiometric test, which may invoke the testing module 208 of FIG. 2 and result in the display of the user interface 802 show in FIG. 8. In some embodiments, the user interface 802 may only include a single button 804 or other central or prominent control indicating that the user heard the generated tone.

FIG. 8 also includes a dataflow and timing diagram showing the flow of data between the mobile device 104 and the audiometer 102. Initially, the mobile device 104 sends a first structured message 806 instructing the audiometer 102 to play a tone of a certain frequency and a certain decibel level in particular ear of the subject. For example, the first structured message 806 may include a Bluetooth command/message (packet) and may instruct the audiometer 102 to pay a 1000 Hz tone at 60 dB in the subject's left ear (i.e., in the left driver of the headset 112).

The audiometer 102 begins the tone at point 808 and ends the tone at point 810. The audiometer 102 sends a second structured message 814 (e.g., Bluetooth packet) to the mobile device 104 indicating that the tone has been played. When the second structured message 814 is received, the mobile device 104 begins a timer at point 816. The timer may proceed for a predetermined amount of time, e.g., 400 milliseconds.

If the subject presses the button 804 at point 818 before the timer ends at point 820, a success is registered at point 822. If, however, the subject presses the button 804 at point 824 after the timer ends at point 820, an error is registered at point 826. As previously noted, the test may be conducted according to the Hughson-Westlake procedure, in which the threshold of hearing is defined as 2 out of 3 (or 3 out of 5) correct responses (successes) during the ascending portion of the tone presentation. If the patient responds when the tone is ascending, the test will automatically decrease the level by 10 dB. The patient has to respond to the same intensity 2 out of 3 or 3 out of 5 times for the threshold to be recorded. Intensity increases will be in steps of 5 dB while the intensity decreases will be in steps of 10 dB.

The time between tones (and, hence, messages 806 from the mobile device 104) may vary within a particular range (e.g., 720 to 2000 milliseconds) in order to prevent the subject from anticipating the timing of the tones. As such, messages 806 from the mobile device 104 may be delayed or timed within the particular range by a random factor.

Accordingly, multiple tones are generated in each ear of the subject using a series of frequencies, e.g., 500 Hz, 1000 Hz, 2000 Hz, 3000 Hz, 4000 Hz, and 8000 Hz. In effect, when the subject fails to indicate that the particular tone has been heard within a predetermined time interval, the sound pressure level for the missed tone will be progressively increased (although not necessarily in a sequential fashion) until the subject has indicated that the particular tone has been heard within the predetermined time interval. In other words, the audiometric test determines how loud sounds need to be at different frequencies in order for the subject to hear them.

Figure 9:
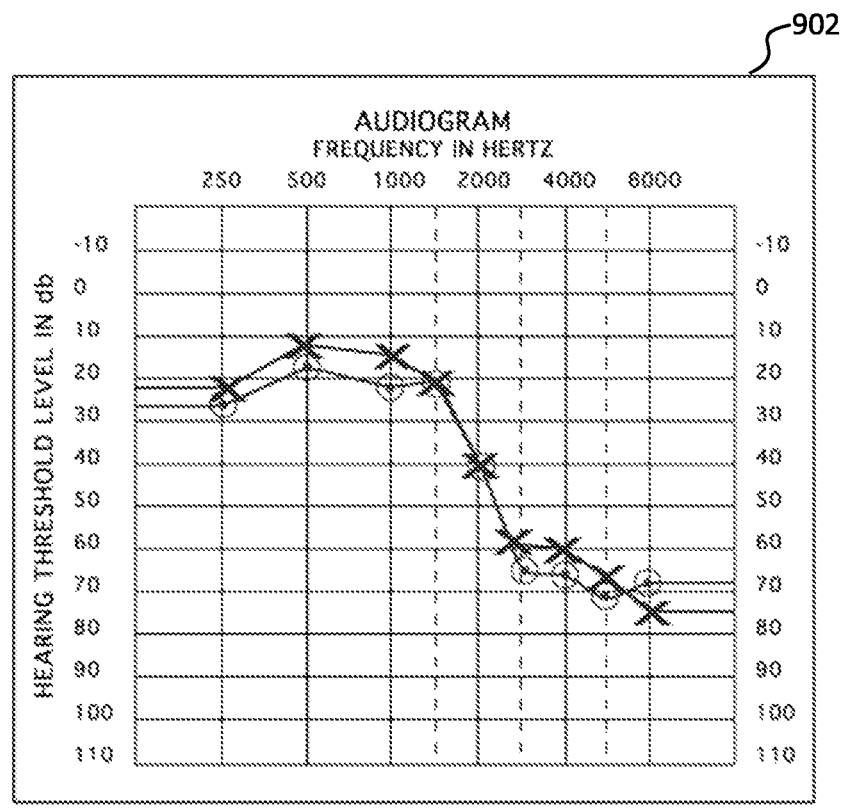
FIG. 9 is an exemplary audiogram according to an embodiment.

It is possible that user responses may result in an invalid test notwithstanding the fact that the room and audiometer/headset have been validated and the subject has been properly instructed. For example, the subject may provide inconsistent responses or too frequently "hear" tones that have not been played. However, as shown in FIG. 9, assuming that hearing threshold levels can be determined, test results including, for example, an audiogram 902, may be generated by the reporting module 210. In the audiogram 902, the lines plotted by X's represent the hearing threshold levels for the subject's left ear, while the lines connected by O's represent the hearing thresholds for the subject's right ear.

The reporting module 210 may electronically report the results of the audiometric test, which may include sending at least one of an email or a text message containing or referencing (e.g., via a link) the audiogram 902 to one or more of the subject and an employer of the subject. In some embodiments, the reporting module 210 will verbally explain the results to the subject using text-to-speech, sampled audio, artificial intelligence (AI) and/or other suitable technologies.

Figure 10:
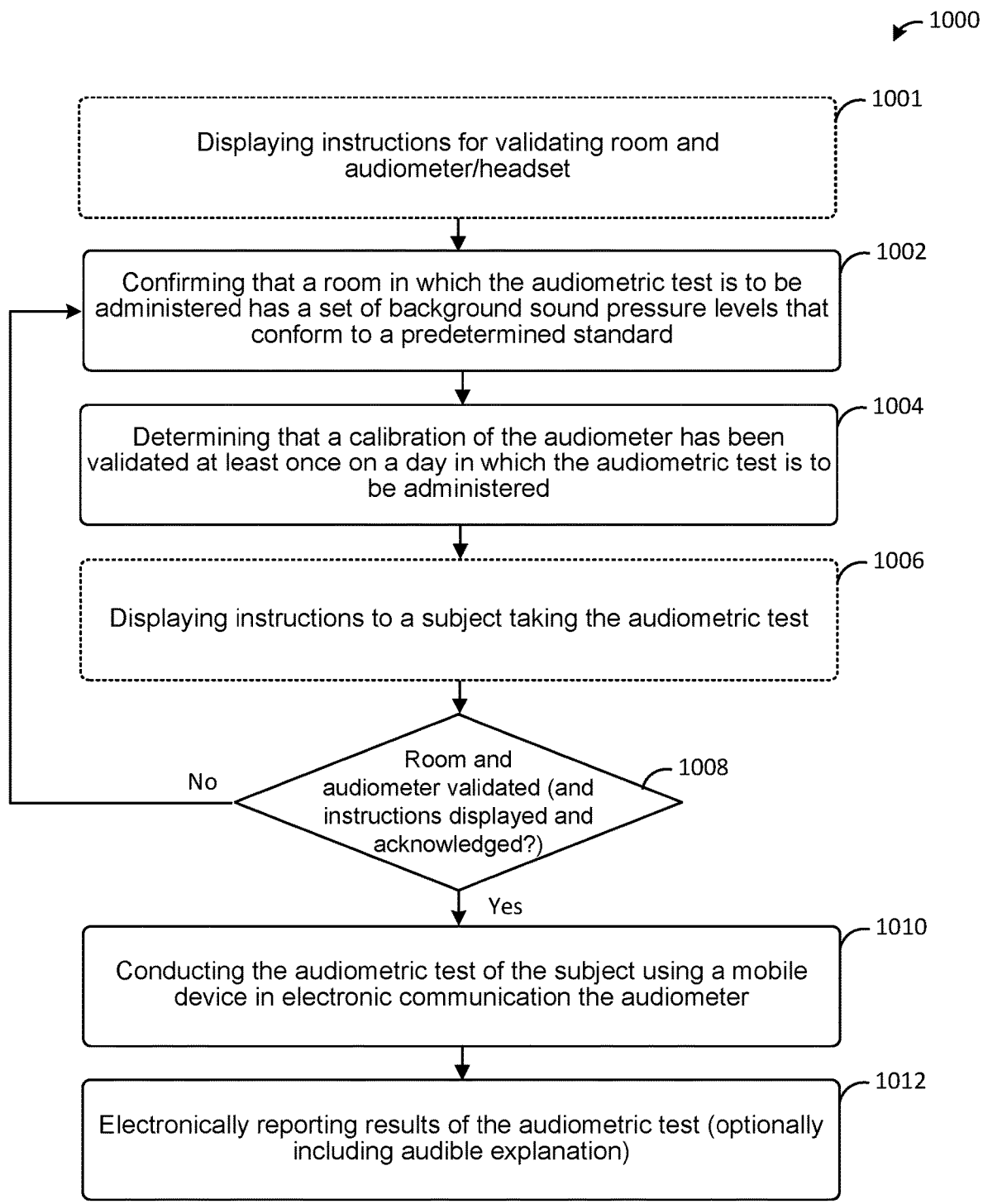
FIG. 10 is a flowchart of a method for conducting an audiometric test according to an embodiment.

FIG. 10 is a flowchart of a method 1000 for conducting an audiometric test. The method optionally begins at step 1001 by displaying instructions for validating the room and/or audiometer/headset as previously described. The instructions may be displayed to a proctor (test administrator) or the subject. In some embodiments, displaying the instructions is a prerequisite to conducting the audiometric test.

The method 1000 continues at step 1002 by confirming that a room in which the audiometric test is to be administered has a set of background sound pressure levels that conform to a predetermined standard. In one embodiment, this may be done by sampling the set of background sound pressure levels at each of the plurality of octave-band center frequencies using the audiometer 102. The plurality of octave-band center frequencies are selected from the group consisting of 500 Hz, 1000 Hz, 2000 Hz, 4000 Hz, and 8000 Hz, and the corresponding maximum sound pressure levels for the plurality of octave-band center frequencies are selected from the group consisting of 40 dB at 500 Hz, 40 dB at 1000 Hz, 47 dB at 2000 Hz, 57 dB at 4000 Hz, and 62 dB at 8000 Hz.

At step 1004, the method 1000 continues by determining that a calibration of the audiometer 102 and headset 112 has been validated at least once on a day in which the audiometric test is to be administered. In one embodiment, the audiometer 102 includes a tone generator 116 electronically connected to a headset 112 and, in response to determining that the calibration the audiometer has not been validated at least once on the day in which the audiometric test is to be administered, the method 1000 may include sampling audio output of the headset at each a plurality of test tones generated by the tone generator and determining that the audio output of the headset deviates from each of the plurality of test tones by no more than a threshold decibel level.

Optionally, at step 1006, the method 1000 may continue by displaying instructions 404 to a subject for taking the audiometric test. In one embodiment, a training video 406 demonstrating one or more of the instructions to the subject may be displayed. Furthermore, in one embodiment, the audiometric test cannot proceed until confirmation from the subject regarding the instructions has been received.

At step 1008, a determination is made whether the room and audiometer 102 (including the headset 112) and have been validated in steps 1002 and 1004 and (optionally) whether the instructions have been displayed (and acknowledged) in step 1006. If not, the method returns to step 1002; otherwise, the method continues at step 1010 by conducting the audiometric test of the subject using the mobile device 104, where the mobile device is separate from and controls the audiometer. The audiometric test may be conducted using the mobile device 104 to perform the logic of the test (using, for example, the Hughson-Westlake procedure) while controlling the audiometer 102 via structured messages (e.g., Bluetooth packets) to generate the tones.

At step 1012, the method continues by electronically reporting results of the audiometric test. For example, the results may be sent using at least one of an email or a text message containing or referencing the results to one or more of the subject and an employer of the subject. The results may be in the form of an audiogram that includes, for each ear of the subject, a graph of hearing threshold levels of the subject for a set of frequencies. Optionally, the results may include a spoken explanation of the test results, which may be generated using text-to-speech or other technologies. In some cases, such as where the subject's hearing has changed from a prior test or where the subject's hearing is below a predetermined standard, the explanation of the test results may need to be provided in order to satisfy certain testing standards.

Data regarding room validation, audiometer/headset validation, instruction of the subject, and reporting (including a spoken or otherwise delivered explanation to the subject) may be logged in the memory 114 or another suitable location for subsequent certification of the audiometric by a test administrator, employer, or third party (e.g., government agency).

The system 100 described above has many advantages over conventional approaches. The audiometer 102 and mobile device 104 may be small and light, making it possible to easily transport the system 100 to different testing sites. Furthermore, the system 100 uses relatively inexpensive components and may be easily repaired if either the audiometer 102 or the mobile device 104 is damaged. Finally, the system 100 produces valid audiometric tests by requiring room validation, audiometer/headset validation, and/or proper instruction of the subject, before the audiometric test may commence, providing the ability to certify that an audiometric test and its accompanying results are valid and correct.

As used herein, the articles "a" and "an" refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

The present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

The systems and methods described herein can be implemented in hardware, software, firmware, or combinations of hardware, software and/or firmware. In some examples, systems described in this specification may be implemented using a non-transitory computer-readable medium storing computer-executable instructions (e.g., program code) that when executed by one or more processors of a computer cause the computer to perform operations (e.g., methods, processes). Computer-readable media suitable for implementing the control systems described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer-readable medium that implements a control system described in this specification may be located on a single device or computing platform or may be distributed across multiple devices or computing platforms.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A system for conducting an audiometric test of a subject, the system comprising:
   an audiometer; and
   a mobile device in electronic communication with the audiometer, wherein the audiometer and the mobile device are separate devices, and the mobile device includes:
      a display screen;
      one or more processors; and
      a memory storing program code that causes the one or more processors to:
         confirm that a room in which the audiometric test is to be administered has a set of background sound pressure levels that conform to a predetermined standard;
         determine that a calibration of the audiometer has been validated at least once on a day in which the audiometric test is to be administered; and
         conduct the audiometric test of the subject using the audiometer under control of the mobile device, wherein conducting the audiometric test is prevented until the one or more processors have confirmed that the room in which the audiometric test is to be administered has the set of background sound pressure levels that conform to the predetermined standard and that the calibration of the audiometer has been validated at least once on the day in which the audiometric test is to be administered,
   wherein the audiometer includes a tone generator electronically connected to a headset, and wherein the one or more processors, in response to the calibration of the audiometer not having been validated at least once on the day in which the audiometric test is to be administered, are to sample audio output of the headset at each a plurality of test tones generated by the tone generator and determine that the audio output of the headset deviates from each of the plurality of test tones by no more than a threshold decibel level.

2. The system of claim 1, wherein the predetermined standard for the room includes a plurality of octave-band center frequencies and corresponding maximum sound pressure levels, and wherein the one or more processors are to confirm that the room in which the audiometric test is to be administered has the set of background sound pressure levels that conform to the predetermined standard by confirming that the set of background sound pressure levels at each of the plurality of octave-band center frequencies do not exceed the corresponding maximum sound pressure levels.

3. The system of claim 2, wherein the one or more processors are to confirm that the set of background sound pressure levels at each of the plurality of octave-band center frequencies do not exceed the corresponding maximum sound pressure levels by sampling the set of background sound pressure levels at each of the plurality of octave-band center frequencies using the audiometer.

4. The system of claim 3, wherein the plurality of octave-band center frequencies are selected from the group consisting of 500 Hz, 1000 Hz, 2000 Hz, 4000 Hz, and 8000 Hz.

5. The system of claim 4, wherein the corresponding maximum sound pressure levels for the plurality of octave-band center frequencies are selected from the group consisting of 40 dB at 500 Hz, 40 dB at 1000 Hz, 47 dB at 2000 Hz, 57 dB at 4000 Hz, and 62 dB at 8000 Hz.

6. The system of claim 1, wherein further comprising a calibrator including:
   a housing; and
   two microphones positioned on opposite sides of the housing and configured to be placed in proximity to respective drivers of the headset when the audio output of the headset is being sampled.

7. The system of claim 1, wherein the threshold decibel level is 10 dB, and wherein the plurality of test tones have frequencies selected from the group consisting of 500 Hz, 1000 Hz, 2000 Hz, 3000 Hz, 4000 Hz, 6000 Hz, and 8000 Hz.

8. The system of claim 1, wherein the one or more processors are to display, on the display screen, instructions to a subject for taking the audiometric test.

9. The system of claim 8, wherein the one or more processors are further to receive confirmation from the subject that the instructions have been viewed, and wherein the one or more processors are to prevent conducting the audiometric test until the confirmation from the subject has been received.

10. The system of claim 1, wherein the one or more processors are to conduct the audiometric test by:
   sending a first structured message from the mobile device to the audiometer instructing the audiometer to generate a tone at a predetermined frequency;
   receiving a second structured message at the mobile device from the audiometer indicating that the tone has been generated;
   determining at the mobile device whether the subject has indicated that the tone has been heard within a predetermined time interval; and
   repeating the steps of sending, receiving, and determining at each of a plurality of predetermined frequencies for each ear of the subject.

11. The system of claim 10, wherein the one or more processors are further to progressively increase a sound pressure level of a particular tone, in response to the subject failing to indicate that the particular tone has been heard within the predetermined time interval, until the subject has indicated that the particular tone has been heard within the predetermined time interval.

12. The system of claim 10, wherein the plurality of predetermined frequencies are selected from the group consisting of 500 Hz, 1000 Hz, 2000 Hz, 3000 Hz, 4000 Hz, 6000 Hz, and 8000 Hz, and wherein the one or more processors are to cause the audiometer to generate tones for each of the plurality of predetermined frequencies for each ear of the subject using a Hughson-Westlake procedure.

13. The system of claim 10, wherein the first structured message and the second structured message comprise Bluetooth packets.

14. The system of claim 10, wherein the one or more processors are to send the first structured message after a delay within a predetermined delay range.

15. The system of claim 14, wherein the delay is determined randomly.

16. The system of claim 10, wherein the one or more processors are further to electronically report results of the audiometric test.

17. The system of claim 16, wherein the one or more processors are to electronically report the results by sending at least one of an email or a text message containing or referencing the results to one or more of the subject and an employer of the subject.

18. The system of claim 16, wherein the one or more processors are to electronically report the results by generating an audiogram that includes, for each ear of the subject, a graph of hearing threshold levels of the subject for a set of frequencies.

19. The system of claim 16, wherein the one or more processors are to generate a spoken explanation of the results using text-to-speech.

20. A computer-implemented method for conducting an audiometric test of a subject using an audiometer, the computer-implemented method comprising:
  confirming that a room in which the audiometric test is to be administered has a set of background sound pressure levels that conform to a predetermined standard;
  determining that a calibration of the audiometer has been validated at least once on a day in which the audiometric test is to be administered; and
  conducting the audiometric test of the subject using a mobile device in electronic communication with the audiometer, wherein the mobile device is separate from and controls the audiometer, and wherein conducting the audiometric test is prevented until the confirming and determining steps have been performed, wherein the audiometer includes a tone generator electronically connected to a headset, and wherein determining comprises:
    in response to the calibration of the audiometer having not been validated at least once on the day in which the audiometric test is to be administered:
      sampling audio output of the headset at each a plurality of test tones generated by the tone generator; and
      determining that the audio output of the headset deviates from each of the plurality of test tones by no more than a threshold decibel level.

21. The computer-implemented method of claim 20, wherein the predetermined standard for the room includes a plurality of octave-band center frequencies and corresponding maximum sound pressure levels, and wherein confirming comprises confirming the set of background sound pressure levels at each of the plurality of octave-band center frequencies do not exceed the corresponding maximum sound pressure levels.

22. The computer-implemented method of claim 21, wherein confirming that the set of background sound pressure levels at each of the plurality of octave-band center frequencies do not exceed the corresponding maximum sound pressure levels comprises sampling the set of background sound pressure levels at each of the plurality of octave-band center frequencies using the audiometer.

23. The computer-implemented method of claim 22, wherein the plurality of octave-band center frequencies are selected from the group consisting of 500 Hz, 1000 Hz, 2000 Hz, 4000 Hz, and 8000 Hz.

24. The computer-implemented method of claim 23, wherein the corresponding maximum sound pressure levels for the plurality of octave-band center frequencies are selected from the group consisting of 40 dB at 500 Hz, 40 dB at 1000 Hz, 47 dB at 2000 Hz, 57 dB at 4000 Hz, and 62 dB at 8000 Hz.

25. The computer-implemented method of claim 20, wherein determining that the audio output of the headset deviates from each of the plurality of test tones by no more than a threshold decibel level is performed by a calibrator including a housing and two microphones positioned on opposite sides of the housing, wherein the two microphones are configured to be placed in proximity to respective drivers of the headset when the audio output of the headset is being sampled.

26. The computer-implemented method of claim 20, wherein the threshold decibel level is 10 dB, and wherein the plurality of test tones have frequencies selected from the group consisting of 500 Hz, 1000 Hz, 2000 Hz, 3000 Hz, 4000 Hz, 6000 Hz, and 8000 Hz.

27. The computer-implemented method of claim 20, further comprising displaying, on a display screen, instructions to a subject for taking the audiometric test.

28. The computer-implemented method of claim 27, further comprising receiving confirmation from the subject that the instructions have been viewed, and wherein conducting the audiometric test is prevented until the confirmation from the subject has been received.

29. The computer-implemented method of claim 20, wherein conducting the audiometric test comprises:
  sending a first structured message from the mobile device to the audiometer instructing the audiometer to generate a tone at a predetermined frequency;
  receiving a second structured message at the mobile device from the audiometer indicating that the tone has been generated;
  determining at the mobile device whether the subject has indicated that the tone has been heard within a predetermined time interval; and
  repeating the steps of sending, receiving, and determining at each of a plurality of predetermined frequencies for each ear of the subject.

30. The computer-implemented method of claim 29, further comprising progressively increasing a sound pressure level of a particular tone, in response to the subject failing to indicate that the particular tone has been heard within the predetermined time interval, until the subject has indicated that the tone has been heard within the predetermined time interval.

31. The computer-implemented method of claim 29, wherein the plurality of predetermined frequencies are selected from the group consisting of 500 Hz, 1000 Hz, 2000

Hz, 3000 Hz, 4000 Hz, 6000 Hz, and 8000 Hz, and wherein conducting the audiometric test comprises conducting the audiometric test using a Hughson-Westlake procedure.

32. The computer-implemented method of claim 29, wherein the first structured message and the second structured message comprise Bluetooth packets.

33. The computer-implemented method of claim 29, wherein sending comprises sending the first structured message after a delay within a predetermined delay range.

34. The computer-implemented method of claim 33, wherein the delay is determined randomly.

35. The computer-implemented method of claim 29, further comprising electronically reporting results of the audiometric test.

36. The computer-implemented method of claim 35, wherein electronically reporting the results comprising sending at least one of an email or a text message containing or referencing the results to one or more of the subject and an employer of the subject.

37. The computer-implemented method of claim 35, wherein electronically reporting the results comprises generating an audiogram that includes, for each ear of the subject, a graph of hearing threshold levels of the subject for a set of frequencies.

38. The computer-implemented method of claim 35, wherein electronically reporting comprises electronically generating a spoken explanation of the results using text-to-speech.

39. A non-transitory computer-readable medium storing program code that, when executed by one or more processors, cause the one or more processors to perform a method for conducting an audiometric test of a subject using an audiometer, the method comprising:

confirming that a room in which the audiometric test is to be administered has a set of background sound pressure levels that conform to a predetermined standard;

determining that the audiometer has been calibrated at least once on a day in which the audiometric test is to be administered; and conducting the audiometric test of the subject using a mobile device in electronic communication the audiometer, wherein the mobile device is separate from and controls the audiometer, and wherein conducting the audiometric test is prevented until the steps of confirming and determining have been performed, wherein the predetermined standard for the room includes a plurality of octave-band center frequencies and corresponding maximum sound pressure levels, and wherein confirming comprises confirming the set of background sound pressure levels at each of the plurality of octave-band center frequencies do not exceed the corresponding maximum sound pressure levels, and wherein confirming that the set of background sound pressure levels at each of the plurality of octave-band center frequencies do not exceed the corresponding maximum sound pressure levels comprises sampling the set of background sound pressure levels at each of the plurality of octave-band center frequencies using the audiometer.

* * * * *